(12) United States Patent
Wang et al.

(10) Patent No.: US 8,409,116 B2
(45) Date of Patent: Apr. 2, 2013

(54) METHOD AND DEVICE TO MANAGE FREEZING OF GAIT IN PATIENTS SUFFERING FROM A MOVEMENT DISORDER

(75) Inventors: Emily Wang, Chicago, IL (US); Leonard Verhagen Metman, Chicago, IL (US); Emil Jovanov, Huntsville, AL (US)

(73) Assignee: Rush University Medical Center, Chicago, IL (US)

( * ) Notice: Subject to any disclaimer, the term of this patent is extended or adjusted under 35 U.S.C. 154(b) by 545 days.

(21) Appl. No.: 12/764,691

(22) Filed: Apr. 21, 2010

(65) Prior Publication Data

US 2010/0274304 A1 Oct. 28, 2010

Related U.S. Application Data

(60) Provisional application No. 61/171,751, filed on Apr. 22, 2009.

(51) Int. Cl.
*A61B 5/00* (2006.01)

(52) U.S. Cl. .................................................. 600/595
(58) Field of Classification Search .............. 600/587, 600/595; 607/45, 48, 49
See application file for complete search history.

(56) References Cited

U.S. PATENT DOCUMENTS

| 5,575,294 | A | 11/1996 | Perry et al. |
| 7,369,896 | B2 | 5/2008 | Gesotti et al. |
| 2006/0100546 | A1 | 5/2006 | Silk |
| 2008/0004904 | A1 | 1/2008 | Tran |
| 2008/0186189 | A1 | 8/2008 | Azzaro et al. |

OTHER PUBLICATIONS

Hutton, Thomas J. M.D. Ph.D,, "Combating Mobility Freezing Caused by Parkinson's Disease", http://www.grandtimes.com/Combating_Mobility.html, 2pgs.
Search Report for Int. App. No. PCT/US2010/031928.

*Primary Examiner* — Max Hindenburg
(74) *Attorney, Agent, or Firm* — Husch Blackwell LLP

(57) ABSTRACT

The subject invention involves a device and method for treating patients with a movement disorder experiencing a sudden change in regularity of gait or akinesia, and comprising a device that detects the sudden change in regularity of gait or temporary akinesia and automatically issues a cue signal that restarts the movement.

19 Claims, 2 Drawing Sheets

METHOD AND DEVICE TO MANAGE FREEZING OF GAIT IN PATIENTS SUFFERING FROM A MOVEMENT DISORDER

BACKGROUND

A device and method for treating patients with movement disorder associated akinesia is described.

A movement disorder is a neurological disturbance of motor control that leads to abnormal movement. Movement disorders include Parkinson's disease (PD), Huntington's disease, atypical Parkinsonism such as progressive supranuclear palsy (PSP) and Multisystem atrophy (MSA), Wilson's disease, Tourette's syndrome and various chronic tremors. The secondary effects of stroke may also be included in this list even though stroke itself is not considered a movement disorder. Different clinically observed movement disorders can be traced to the same or similar areas of the brain.

Freezing of gait (FOG) is a common complication in movement disorders (e.g. 80% of PD patients), and leads to falls and injuries. Walking difficulties in these movement disorders may include shuffling, festination and akinetic episodes, which are popularly referred to as freezing. Akinesia means partial or complete loss of movement. Relative to Parkinsonism, akinesia usually denotes the sudden inability to initiate movement. Arms and hands may become momentarily akinetic, but much more commonly the feet/legs become akinetic or freezing. These freezing episodes present a distressing problem for the individual and impair their ability to walk normally.

PD is a chronic, progressive, neurodegenerative disorder resulting from the selective degeneration of specific brain cells of the substantia nigra. The incidence of PD is reported as 1% of the population over the age of 50, and as high as 10% over the age of 65. There are over 1.5 million persons with PD in the United States. Clinical presentation of the disease includes resting tremor, rigidity, bradykinesia or akinesia, and loss of postural reflexes.

FOG responds poorly to pharmacological and surgical treatment. FOG has been linked to diminished internally generated movement cues due to the damage to the basal ganglia. Externally provided auditory rhythmic cues have been shown to influence movement speed in patients with FOG. However, problems remain when patients tried to synchronize to the cueing frequencies and the training effects were not sustained once the cues were removed.

Everyday, PD patients with FOG are at risk of falls and injuries. It affects their quality of life and the lives of their loved ones. The falls and injuries can impact them financially. The risk of falls and injuries can increase the anxiety level in the patients and their families. Since FOG does not respond to pharmacological and surgical treatment and FOG can occur both during the "on" and "off" medication period, finding an effective, easy-to-use, low cost and reliable way to resolve the FOG becomes very urgent.

Usually, FOG is associated with the advanced stages of PD (stage 3, 4, or 5) but it can also be present earlier in the disease course when balance is still intact. Individuals have described their feet as suddenly being "stuck", "glued" or "cemented" to the floor for brief (seconds) or longer (minutes) periods of time. This happens spontaneously while they are walking or as they begin walking (start-hesitation) with little warning. Some people are prone to FOG when they approach a narrow space, threshold or doorway. FOG may occur once or several times in succession during a short walk, and the incidence of episodes may vary from day to day. FOG and/or start-hesitation impedes free mobility and, as the disease progresses, increases the risk of falling.

People have attempted to manage FOG in various ways. The scientific basis for the management techniques usually involve providing some visual cue which encourages the feet to step up and over, as if unsticking from glue, rather than stepping forward, as with regular walking. These tricks are usually taught in the physician's office by the doctors, nurses and therapists who are familiar with the symptom. People also learn the methods from reading books about PD or by attending support group meetings. One technique that some use is to move to sound cues such as marching music or counting. Another method is to draw an imaginary line in front of the afflicted person's feet and encourage the patient to step up and over the imaginary line. Also used is the dropping or placing of objects (e.g. paper, tissue, straws, belts, etc.) on the floor in front of the person's feet; forcing them to step over the object.

The aforementioned interventions have been helpful to people, but each has drawbacks. Dropping or placing items of the floor requires not only that you have the objects ready to use but also that someone be available to place and retrieve the objects. One alternative to this is to use small disposable objects (e.g., cards) and leave the object(s) behind. With other objects, if the object is 3-dimensional, such as a belt, the individual could trip and fall. The imaginary line method works well, but again, someone usually must accompany the individual to draw the line with their foot or hand. Some patients find it difficult to imagine a line during the FOG episode and remain unable to move until involuntary release occurs. Sound cues (such as marching music) are not often feasible, particularly outside the home, and many find singing or counting aloud embarrassing. Often, a PD patient will just sit down and stop what he or she is doing. These tricks are some of the only mechanical techniques available to individuals in the United States who suffer from FOG and start-hesitation and they are often impractical for daily use.

More modern devices that have been developed to manage FOG include a projection device that projects a thin beam or discrete pattern of light using a laser, flash or other high-intensity light source to provide a luminous mark in the path of a standing individual (U.S. Pat. No. 5,575,294). This is a visual cue similar to the tricks described above and overcomes some of the problems inherent for such cues. It can be used alone or adapted to an assistive support such as a cane or walker, or to an item of clothing. It still requires the user to activate the device and does not automatically activate when FOG has been detected. If the user has akinesia in the arms and hands, the device is limited in its usefulness.

To overcome the user activated problem, Gesotti (U.S. Pat. No. 7,369,896) has developed movement timing stimulator systems and methods. The system including one or more motion sensors adapted to detect one or more movement parameters of a patient, a control panel, a plurality of customized parameter setting menu, and an over voltage/current monitoring circuit. The system further includes a controller that receives signals from the one or more motion sensors, control panel, customized parameter setting menus, and monitoring circuit and determines when stimulation prompts are required for a desired treatment of symptoms and a plurality of cutaneous stimulation electrodes placed in the vicinity of motor points for timed periodic stimulation prompts, wherein the stimulation prompts are sequentially applied based on the desired treatment of symptoms. The plurality of stimulation prompts is produced using multiple stimulation channels and each stimulation channel is associated with a cue clock. This system is complex, difficult for a user to place on the body and uses stimulation prompts that are electrical in nature. The system does not trick the user to move but "shocks" the user into movement, with the subsequent risks associated with such stimulation.

Thus, there is a need in the art for safe, reliable and simple methods to treat patients faced with FOG and improve outcomes. The methods should provide continuous use and should not be so complicated that caregivers will reject their use. Other objects, features and advantages of the present invention will become apparent from the following detailed description. It should be understood, however, that the detailed description and the specific example, while indicating preferred embodiments of the invention, are given by way of illustration only, since various changes and modifications within the spirit and scope of the invention will become apparent to those skilled in the art from the detailed description.

SUMMARY OF THE INVENTION

In accordance with the subject invention a freezing gait disorder is treated or managed by a wearable device that detects the change in regularity of gait or akinetic movement within a fraction of a second, sending a signal to a receiver which automatically emits a cue signal. The cue signal resolves the freezing and thus helps the person initiate movement.

DETAILED DESCRIPTION OF THE INVENTION

The instant invention is a novel digital device that manages a freezing gait disorder by detecting the moment of FOG and automatically provides an auditory cue at the moment of FOG. This system consists of two components. The main component is a gait sensor with digital transmitter and is preferably smaller than a pager and attached onto a user's belt, pants or dress in the back, similar to the way one wears a pedometer. The same device might be applied on a shoe or in a shoe (e.g. integrated into sole of the shoe), or wrapped above the ankle, or knee according to the user's preference or anywhere else on the user's clothing or body as practical. The other component is a wireless or wired receiver (e.g. widely used Bluetooth® headset) that communicates with the gait sensor.

A preferred cue is the verbal command "WALK." Other preferred acoustic cues may include other verbal commands, rhythmic sounds such as drumming, music or music samples such as "I'm Walking" by Fats Domino or some other repetitive upbeat sound or phrase. Alternatively, other cues such as auditory, tactile, vibration, pressure, thermal or electric stimulation, or a combination of multiple cues, may be used.

Figure 1:
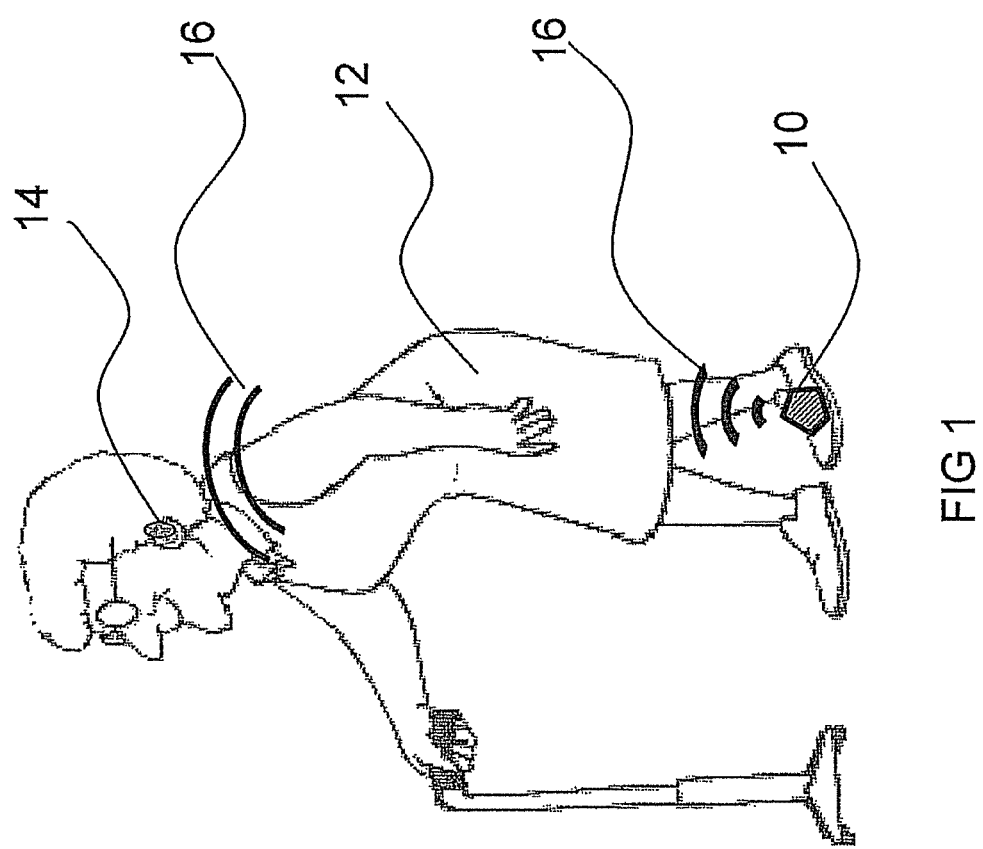
FIG. 1 shows the device in use by a patient.

In FIG. 1, the device is shown as it is used by the patient. The main component, a gait sensor, 10 is attached via attachment means to the user 12. The size of the walking sensor 10 in FIG. 1 is exaggerated for easier viewing but is preferably no larger than a standard sized pager and may be much smaller. In a preferred embodiment, the attachment means is a clip or pin that can be connected to the user's shoe, belt, belt loops or pant waist. In an alternate embodiment, the walking sensor 10 is placed in a carrier made of plastic, fabric, leather or other appropriate materials and the carrier is then attached via a clip, pin or Velcro tape to a shoe (or placed in a shoe), the waist of the user's pants/dress or another appropriate location on the user's body. Still other alternate attachment means can be contemplated by one of ordinary skill in the art. The receiver 14 is preferably a wireless device such as a Bluetooth® headset (e.g. Motorola H780 Bluetooth® headset) and is attached to the user's ear. Alternate receivers 14 can include wired or wireless headphones, ear buds or similar devices. Alternatively, the receiver 14 might be attached directly to mastoid bone and generate vibration as a cue. The gait sensor 10 detects the moment of FOG, i.e., senses the change in regularity in the gait or akinetic episode, and transmits a wireless signal 16 to the receiver 14, which receives the signal, decodes it, and activates a transducer based on the decoded signal, or other cue generator, which emits an auditory or other types of cueing signal, such as verbal or tactile signal, triggering the user 12 to begin walking. In a preferred embodiment, a single gait sensor 10 is used; however, it is contemplated that multiple gait sensors 10 may be used. In an alternate embodiment, the signal may be transmitted through a wire connected to the sensor and receiver. Another implementation might include a gait sensor in the headset to allow a single device implementation. Also the signal may be transmitted to a caregiver nearby or at a remote location.

In case falls do occur after the FOG, information about the event could be sent wirelessly to the caregiver and/or emergency contact and the data included into a personal health record.

Upon perceiving the cue signal at the moment of freezing, the user 12 will initiate walking, resolving the FOG. A verbal (e.g., walk!) cue works better because it activates the same cortical representation of the body parts that need to carry out the action. The use of an instantaneous cue at the moment of FOG will provide salient sensory information which triggers alternative routes to allow PD patients to unfreeze, thus reducing the risk of falls.

Figure 2:
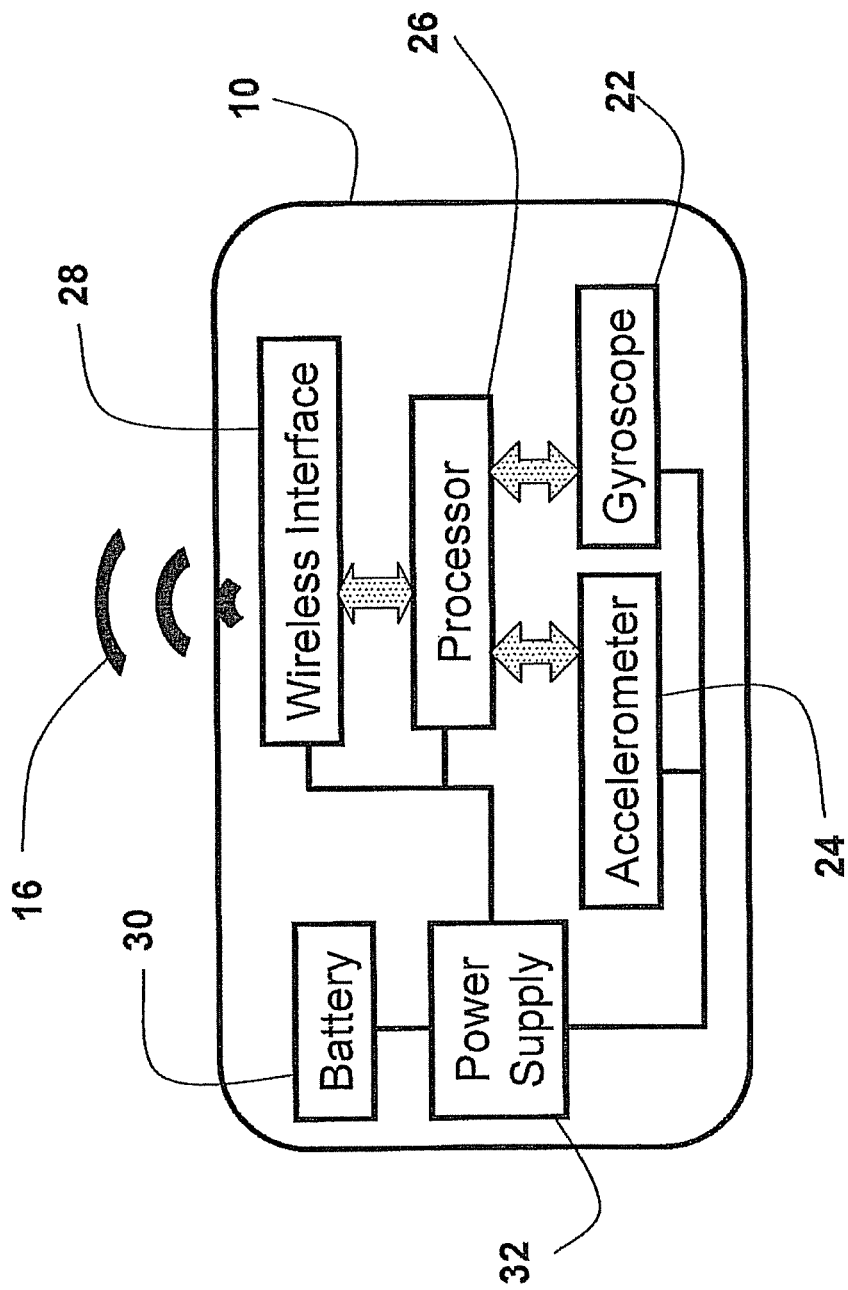
FIG. 2 shows a block diagram of the components of the device.

Turning to FIG. 2, the preferred embodiment of the walking sensor 10 is shown. A two-axis gyroscope 22 (e.g. IDG-500, available from InvenSense™), a three dimensional accelerometer 24 (e.g. Bosch BMA 150, available from Bosch™), a digital signal processor 26 (e.g. MSP430F2274, available from Texas Instruments™), wireless interface 28, battery 30 and a power supply 32 are elements of the unit. The two-axis gyroscope 22 and three-dimensional accelerometer 24 receive mechanical signals (normal gait is stopped) to detect the moment of FOG and send electrical signals to the digital signal processor 26. The FOG event is processed by the digital signal processor 26 to activate the auditory cue and transmit it via the wireless interface 28 to the receiver via a wireless signal 16. Alternative embodiments depend on the capabilities of wireless (or wired) interface used for transmission. The auditory cue can be generated as an analog signal on a digital to analog converter (DAC) of the digital signal processor, or on a separate DAC component programmed by the digital signal processor. The various elements of the device are powered by the power supply 32 which uses any type of battery 30 commonly used in pagers or cell phones, etc. The preferred power supply 32 uses a rechargeable battery 30 (e.g. Lithium Ion or Lithium Polymer) for convenience but the battery 30 may be disposable or any other appropriate form.

In an alternate embodiment, a "kill" switch or power on/off button can be added to the main component so that the user can disable the device when the user is inactive. In a further alternate embodiment, this "kill" switch can be a voice activated component that places the main component in a "sleep" or off mode. A voice activated power switch requires the addition of a receiver to the main component linked to the signal processor which could receive a pre-programmed voice signal from the user (through the Bluetooth® headset) that would be used by the signal processor to enable or disable a switch and power up the unit. An example voice command would be a word or phrase that is not commonly used in every day speech and can include "defog ON" or "defog OFF".

Experiments using a prototype device show that the FOG can be detected in less than 1 second, and the auditory verbal cue helps resolve the FOG.

The subject invention comprises a simple, digital wearable device which will detect the moment of FOG and provide instantaneous auditory help to the patient, and therefore, reducing the risk of falls and injuries. The potential of clinical application is highly significant. The subject invention takes the advantage of the brain activation patterns of action-verbs (e.g., "walk") to use auditory verbal cues instead of auditory rhythmic cues; therefore, it will not require the patients to match their steps to the rhythmic cues. Unlike the rhythmic cues which have to be provided continuously, the verbal cue is provided only when the FOG occurs. The use of the device of the subject invention will not require extensive patient training; therefore, it will reduce the treatment cost, and will benefit both patients with FOG with and without mental declines since it will not require the patients to actively monitor/match the auditory cues.

Although patients with PD are the preferred users of the instant invention, the methods and device described herein are useful in conjunction with other forms of movement disorders which include freeze of gait, or any other disorder involving gait instabilities, thus the instant disclosure should not be read to limit the use of the combination to any one particular form of movement disorder or other disorders involving gait instabilities. Furthermore, the organization and type of the individual elements of the device represent preferred embodiments and should not be read to limit the use of alternate configurations and types. One of ordinary skill in the art can discern, from the description of the instant invention, alternate embodiments that can be contemplated by the designers of the device.

The invention claimed is:

1. A device for treating a human having a movement disorder comprising:
   a sensor for sensing an akinetic episode of said human and a receiver,
   said gait sensor transmitting a signal to said receiver only upon detection of the akinetic episode of said human,
   whereby in response to said received signal, said receiver automatically generates a cueing signal to trigger resumption of movement of said human.

2. The device of claim 1 wherein said sensor comprises one or more accelerometers, or one of more gyroscopes or a combination of both.

3. The device of claim 1 wherein said receiver comprises a wireless headset.

4. The device of claim 1 wherein said receiver includes a wired or wireless headphones or earbuds.

5. A device for emitting a cue upon detecting of change of regularity of gait of a person comprising:
   a sensor for detecting an akinetic episode of the person,
   said sensor including a signal process,
   said signal process sending a signal to a receiver only upon detection of the akinetic episode of the person,
   said receiver, in response to said signal, causing a cue perceptible by the person to be emitted, to thereby aid in the restoration of movement of the person.

6. The device of claim 5 wherein the cue is verbal, auditory, physical or tactile.

7. The device of claim 5 wherein the cue is auditory, tactile, vibratory, pressure, thermal, electric, or a combination thereof can be used.

8. The device of claim 5 wherein the receiver is a wireless headset.

9. The device of claim 5 wherein the sensor includes a gyroscope.

10. The device of claim 5 wherein the receiver includes a cue generator.

11. A method of managing a freezing gait disorder of a person, comprising the steps of:
   sensing a change of regularity of gait of the person,
   transmitting a signal to a receiver only upon sensing the change of regularity of gait,
   automatically generating a cueing signal only upon reception of the signal by said receiver,
   whereby said receiver restarts the gait of said person using single or multiple cues.

12. The method of claim 11 further including the step of transmitting said signal wirelessly.

13. The method of claim 11 including sending a signal wirelessly after sensing the change in regularity of gait of the person.

14. The method of claim 13 including the step of transmitting said signal to a remote location, said signal including an emergency contact and a personal health record.

15. The method of claim 13 including the step of transmitting said signal to a caregiver.

16. The method of claim 11 including the step of generating an auditory cue.

17. The method of claim 11 including generating a tactile cue.

18. The method of claim 11 including generating a verbal cue.

19. The method of claim 11 including transmission of information about FOG events and falls occurring after the FOG, comprising sending the information wirelessly to a caregiver and/or emergency contact, wherein the information includes a personal health record.

* * * * *